United States Patent
Kim

(10) Patent No.: US 9,232,931 B2
(45) Date of Patent: Jan. 12, 2016

(54) ULTRASOUND IMAGING DEVICE AND METHOD FOR CLUTTER FILTERING

(75) Inventor: Tae-Yun Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 347 days.

(21) Appl. No.: 13/092,390

(22) Filed: Apr. 22, 2011

(65) Prior Publication Data
US 2012/0022372 A1 Jan. 26, 2012

(30) Foreign Application Priority Data
Jul. 22, 2010 (KR) .................. 10-2010-0071067

(51) Int. Cl.
*A61B 8/06* (2006.01)
*G01S 15/89* (2006.01)

(52) U.S. Cl.
CPC ............... *A61B 8/06* (2013.01); *G01S 15/8981* (2013.01)

(58) Field of Classification Search
USPC ......................................... 600/437, 441, 457
See application file for complete search history.

(56) References Cited

U.S. PATENT DOCUMENTS

| | | |
|---|---|---|
| 2003/0199764 A1 | 10/2003 | Kim et al. |
| 2004/0199078 A1 | 10/2004 | Mo et al. |
| 2005/0054931 A1 | 3/2005 | Clark |
| 2006/0079782 A1 | 4/2006 | Beach et al. |

FOREIGN PATENT DOCUMENTS

| | | |
|---|---|---|
| EP | 1 067 400 A2 | 1/2001 |
| KR | 2003-0082213 A | 10/2003 |

OTHER PUBLICATIONS

Meagher et al, The Accuracy of Blood Velocity Measurement Using Ultrasound, 2004, IEEE, pp. 535-538.*
Griffin, Mean, Median and Mode Filtering of Images, 2000, The Royal Society, pp. 2995-3004.*
Korean Office Action issued in Korean Patent Application No. 10-2010-0071067 dated Jul. 25, 2012.
Bascom, et al. (1993). On the doppler signal from a steady flow asymmetrical stenosis model: Effects of turbulence. *Ultrasound Med Biol*, 19(3), 197-210.
Ledoux, et al. (1997). Reduction of the clutter component in doppler ultrasound signals based on singular value decomposition: A simulation study. *Ultrasonic Imaging*, 19(1), 1-18.
Tao, et al. (2004). The wall signal removal in doppler ultrasound systems based on recursive PCA. *Ultrasound Med Biol*, 30(3), 369-379.
Yoo, et al. (2003). Adaptive clutter filtering for ultrasound color flow imaging. *Ultrasound Med Biol*, 29(9), 1311-1320.
Yu, et al. (2010). Eigen-based clutter filter design for ultrasound color flow imaging: A review. *IEEE T Ultrason Ferr*, 57(5), 1096-1111.
Yu, et al. (2008). Single-ensemble-based Eigen-processing methods for color flow imaging—part I. The Hankel-SVD filter. *IEEE T Ultrason Ferr*, 55(3), 559-572.
Extended European Search Report issued in European Patent Application No. 11163111.5, dated Nov. 7, 2011.
European Office Communication/Search Report issued in European Application No. 11 163 111.5 dated Sep. 25, 2013.

* cited by examiner

*Primary Examiner* — Rochelle Turchen
(74) *Attorney, Agent, or Firm* — McDermott, Will & Emery LLP

(57) ABSTRACT

An ultrasound imaging device and method for clutter filtering is provided. The ultrasound imaging device provides logic for calculating signal characteristic values from an in-phase/quadrature-phase (I/Q) of an ultrasound signal reflected from an object and determining to remove a clutter element from the I/Q signal through comparison of the calculated signal characteristic values. Accordingly, the ultrasound imaging device provides a blood flow distribution of the object, more precisely visualized, to a user.

2 Claims, 11 Drawing Sheets

| CONDITION | DECISION |
|---|---|
| Mode < Median < Mean | No |
| Mode < Mean < Median | No |
| Median < Mode < Mean | No |
| Mean < Median < Mode | OK |
| Median < Mean < Mode | OK |
| Mean < Mode < Median | OK |

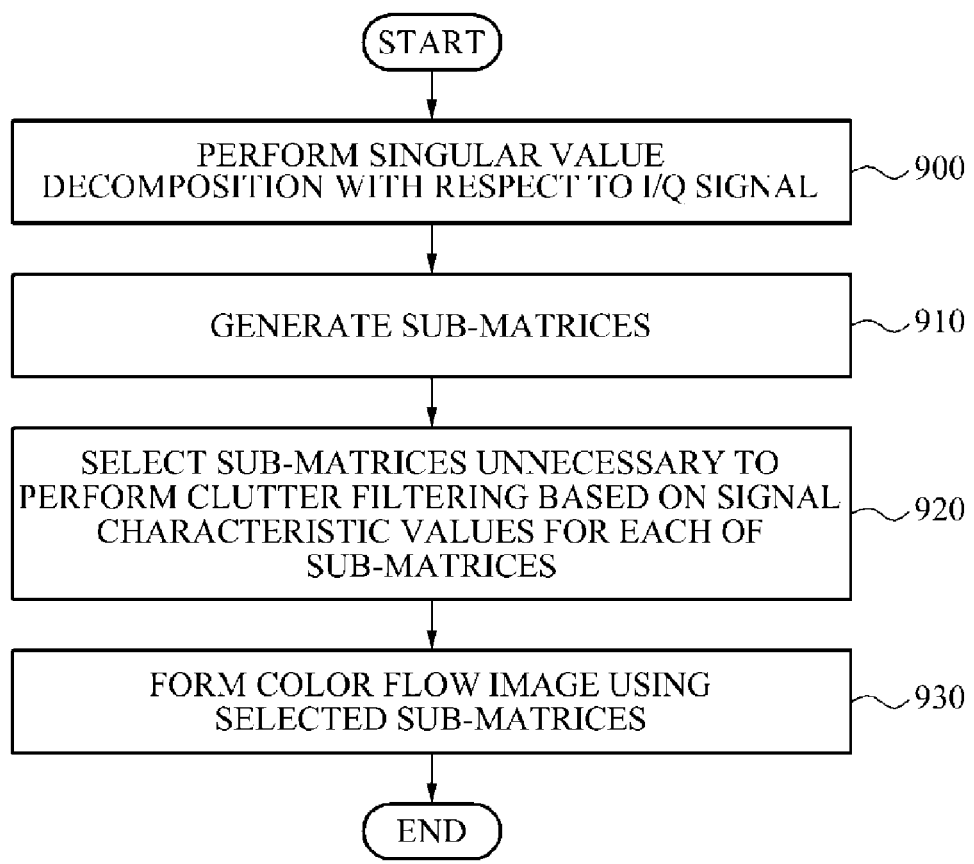

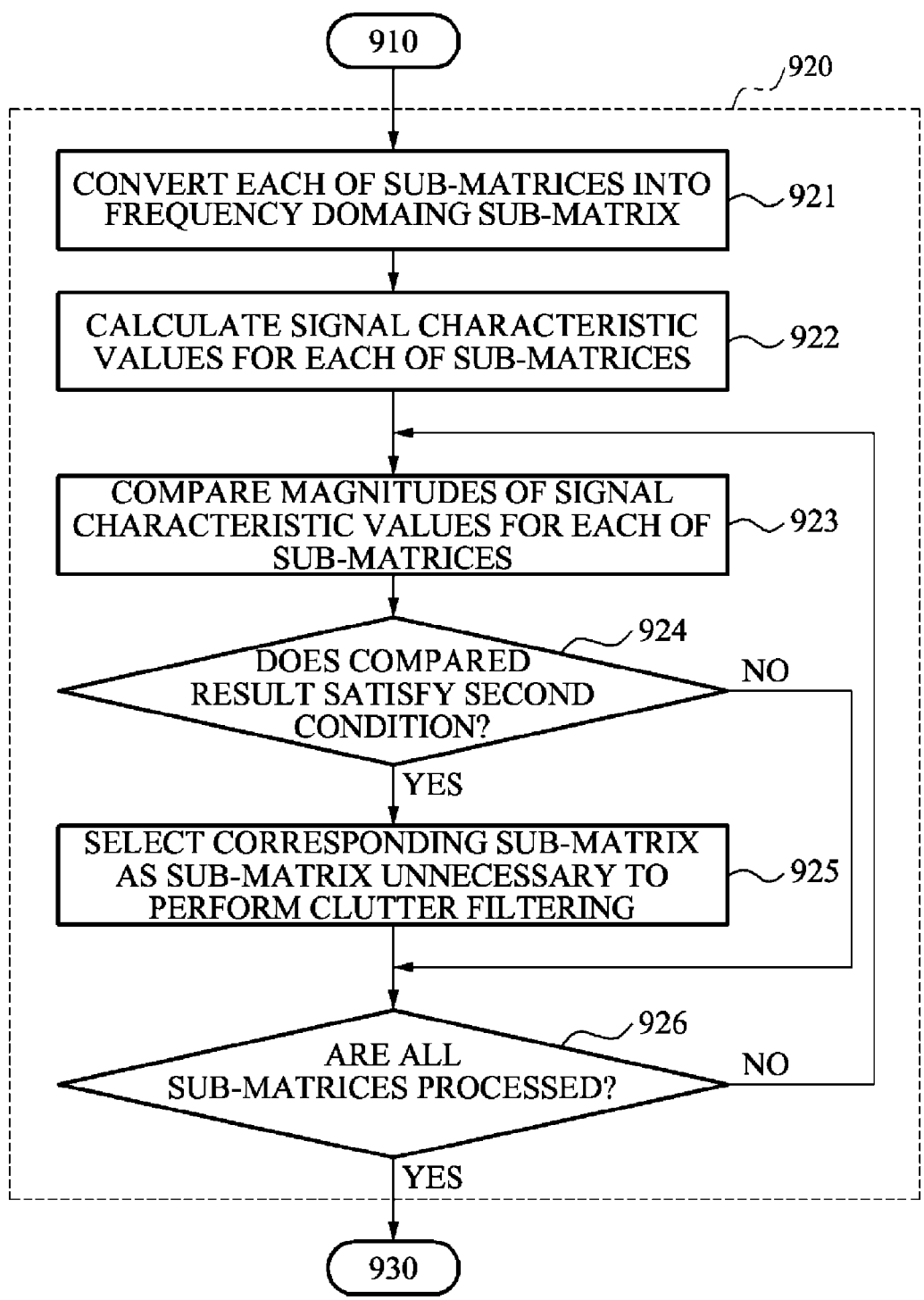

ULTRASOUND IMAGING DEVICE AND METHOD FOR CLUTTER FILTERING

CROSS-REFERENCE TO RELATED APPLICATION

This application claims the benefit of Korean Patent Application No. 10-2010-0071067, filed on Jul. 22, 2010 in the Korean Intellectual Property Office, the disclosure of which is incorporated herein by reference.

BACKGROUND

1. Field of the Invention

The present invention relates to an ultrasound imaging system and method for providing adaptive clutter filtering.

2. Description of the Related Art

An ultrasound imaging device detects and displays distribution of blood flow by irradiating an ultrasound wave onto a human body and measuring the Doppler shift frequency of the ultrasound wave reflected from the blood flow.

Even when the irradiated ultrasound wave is focused and concentrated on the blood flow, a portion of the ultrasound wave is propagated in an undesired direction. As a result, a signal reflected from the blood flow and an undesired signal reflected from elsewhere besides the blood flow are mixed together. In this instance, the signal reflected from the blood flow is referred to as a Doppler signal, and the undesired signal reflected from other tissues is referred to as a clutter signal.

In general, when focusing is performed with an ultrasound wave, most energy is propagated to a focal point, and a portion of the ultrasound wave is leaked to an outside of the focal point. However, although a minute ultrasound wave is generally leaked because the reflectivity of blood flow is significantly smaller than a reflected ultrasound wave of peripheral tissues (blood vessel walls, muscles and the like), an amplitude of a clutter signal almost exceeds an amplitude of a Doppler signal from the blood flow.

Accordingly, many clutter filtering methods exist for conventional ultrasonic systems to effectively remove clutter signals when a color Doppler mode is implemented.

The clutter filtering methods include a method using an infinite impulse response (IIR)-type high-pass filter in which cutoff characteristics are predetermined, an adaptive filtering method for selecting an optical cutoff according to signal characteristics of each pixel, a method for removing clutter signals by decomposing elements of an ensemble data per pixel, and the like.

However, the variance, mean frequency, and power of a signal before the application of clutter filtering are used in most of the clutter filtering methods, or the variance, mean frequency, and power of a decomposed signal are used in most of the clutter filtering methods.

In the present invention, implementation of a decision logic of a clutter filter of converting an in-phase/quadrature-phase (I/Q) signal into a frequency domain signal is performed, and then removal of clutter elements according to the clutter elements signal characteristics is performed.

SUMMARY

An aspect of the present invention provides an ultrasound imaging device and method for adaptively performing clutter filtering by calculating and/or comparing signal characteristic values of an in-phase/quadrature-phase (I/Q) signal.

An aspect of the present invention also provides an ultrasound imaging device and method for forming a color flow image of an ultrasound image by selecting a sub-matrix not used when performing clutter filtering among a plurality of sub-matrices obtained by performing singular value decomposition with respect to an I/Q signal based on signal characteristic values of the I/Q signal.

According to an aspect of the present invention, there is provided an ultrasound imaging device, the device including a signal conversion unit to transmit an ultrasound signal to an object and to receive the ultrasound signal reflected from the object, so as to convert the received ultrasound signal into an I/Q signal corresponding to each pixel of an image in an ultrasound image, and a control unit to converts the I/Q signal into a frequency domain signal and to determine to remove a clutter element from the I/Q signal based on a plurality of signal characteristic values for the converted I/Q signal.

The control unit may generate a plurality of sub-matrices by performing singular value decomposition with respect to the I/Q signal converted by the signal conversion unit and select a sub-matrix that may be disregarded when performing the clutter filtering among the plurality of sub-matrices based on the plurality of signal characteristic values for each of the plurality of sub-matrices. Then, the control unit may form the color flow image of the ultrasound image using the selected sub-matrix.

According to an aspect of the present invention, there is provided an ultrasound imaging method, the method including transmitting an ultrasound signal to an object and converting the ultrasound signal reflected from the object into an I/Q signal, converting the I/Q signal into a frequency domain signal and calculating a plurality of signal characteristic values of the I/Q signal converted into the frequency domain signal, comparing the plurality of signal characteristic values with one another, thereby determining to remove a clutter element from the I/Q signal, and performing clutter filtering with respect to the I/Q signal based on the decision.

According to an aspect of the present invention, there is provided an ultrasound imaging method, the method including transmitting an ultrasound signal to an object and converting the ultrasound signal reflected from the object into an I/Q signal, performing singular value decomposition with respect to the I/Q signal, thereby generating a plurality of sub-matrices, converting each of the plurality of sub-matrices into a frequency domain sub-matrix and calculating a plurality of signal characteristic values for each of the plurality of sub-matrices, comparing the plurality signal characteristic values with one another, thereby selecting a sub-matrix that may be disregarded when removing a clutter element from the I/Q signal among the plurality of sub-matrices, and forming a color flow image of an ultrasound image using the selected sub-matrix.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which:

FIGS. 9 and 10 are flowcharts illustrating an ultrasound imaging method according to another embodiment of the present invention.

DETAILED DESCRIPTION

Figure 1:
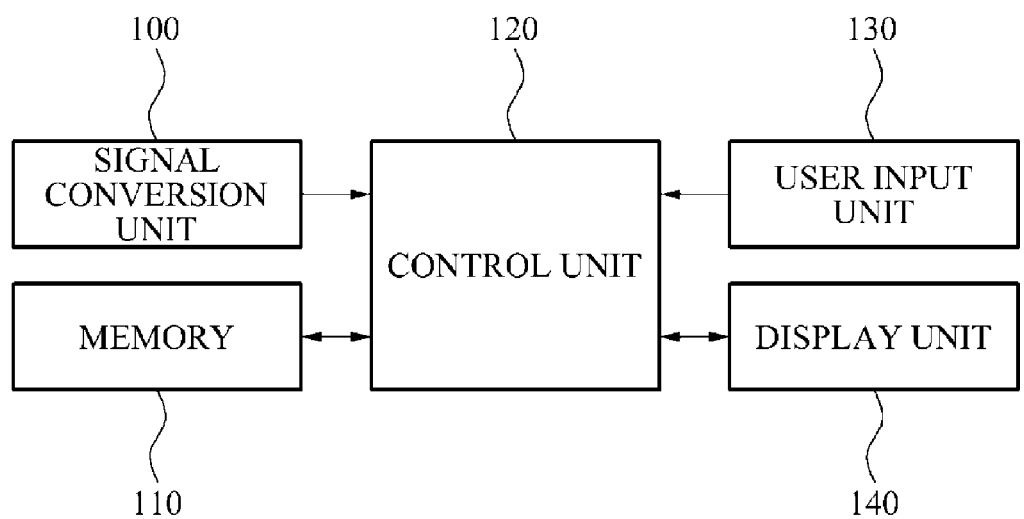
FIG. 1 is a block diagram illustrating a configuration of an ultrasound imaging device according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

FIG. 1 is a block diagram illustrating a configuration of an ultrasound imaging device according to an embodiment of the present invention.

Referring to FIG. 1, the ultrasound imaging device includes a signal conversion unit 100, a memory 110, a control unit 120, a user input unit 130 and a display unit 140.

The signal conversion unit 100 transmits an ultrasound signal to an object and receives an ultrasound signal, that is, an ultrasound echo signal, reflected from the object. Then, the signal conversion unit 100 converts the received ultrasound signal into an in-phase/quadrature-phase (I/Q) signal corresponding to each pixel of an image in an ultrasound image and then outputs the converted I/Q signal. In this instance, a Doppler element and a clutter element are contained together in the I/Q signal.

The signal conversion unit 100 sequentially and repeatedly performs a process of forming a transmission signal based on an ensemble number, thereby generating a plurality of transmission signals. The signal conversion unit 100 converts the generated transmission signal into an ultrasound signal and transmits the converted ultrasound signal to the object. Then, when the reflected ultrasound echo signal is received from the object, the signal conversion unit 100 converts the ultrasound echo signal into a digital signal, and converts the converted ultrasound echo signal in an I/Q signal corresponding to each pixel of the image in the ultrasound image.

The memory 110 stores performing procedures of the ultrasound imaging device. The memory 110 may be implemented as at least one of a general hard disk, random access memory (RAM), and read-only memory (ROM).

The control unit 120 converts the I/Q signal converted and outputted by the signal conversion unit 100 into a frequency domain signal, and determines to remove a clutter element from the I/Q signal based on a plurality of signal characteristic values of the converted I/Q signal.

In this instance, the signal characteristic value may include at least one of a mean value, a median value, and a mode value of the I/Q signal converted into the frequency domain signal.

Thus, the control unit 120 evaluates the amplitude, that is, x-axis frequency and y-axis magnitude, of each frequency element in the I/Q signal outputs a frequency and outputs a frequency having a mean value, a median value, and a mode value.

Here, the mode value refers to a frequency having the maximum magnitude in a fast Fourier transform (FFT) data of the ensemble data. The mode value may be calculated using an FFT order of the ensemble number.

Figures 2A, 2B:
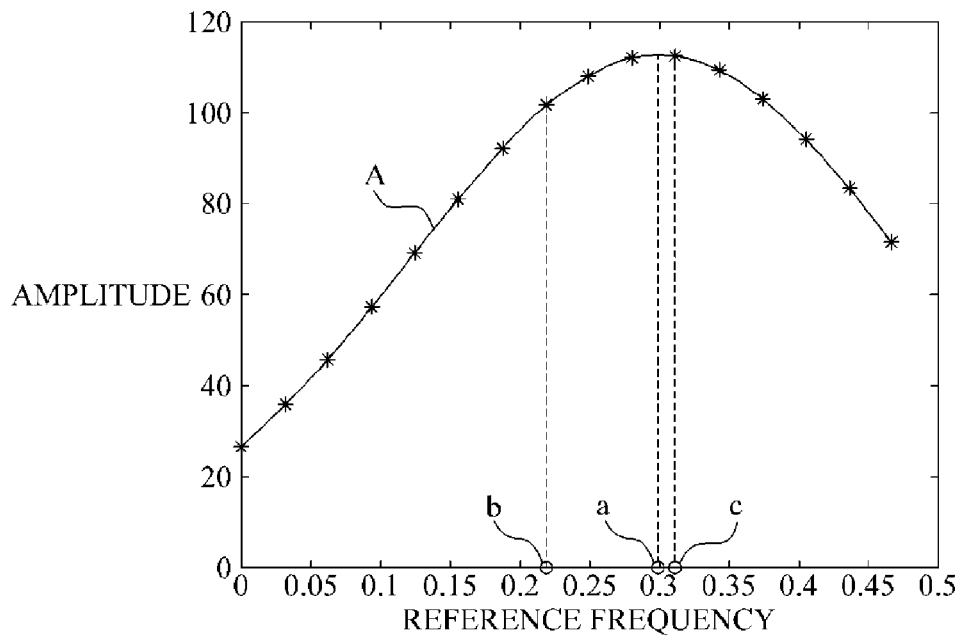
FIG. 2A is a graph illustrating an in-phase/quadrature-phase (I/Q) signal converted into a frequency domain signal in the ultrasound imaging device of FIG. 1 in an ultrasound imaging device according to an embodiment of the present invention.
FIG. 2B is a table illustrating comparative conditions of signal characteristic values calculated in the ultrasound imaging device of FIG. 1.

FIG. 2A is a graph illustrating an I/Q signal converted into a frequency domain signal and its signal characteristic values. FIG. 2B is a table illustrating comparative conditions of the signal characteristic values.

Referring to FIG. 2A, a curve 'A' of an I/Q signal of an arbitrary ensemble number is converted into a frequency domain signal. The mean value of the curve 'A' is 'a', the median value of the curve 'A' is 'b', and the mode value, that is, a number with the highest frequency and the sharpest point in the histogram, of the curve 'A' is 'c'.

The control unit 120 may compare magnitudes of the signal characteristic values as described above and determine to remove a clutter element from the I/Q signal based on the compared result.

Here, conditions of the compared result may be listed as illustrated with reference to FIG. 2B.

Referring to FIG. 2B, in a case where the result obtained by comparing the magnitudes of the plurality of signal characteristic values satisfies any one of [mode<median<mean], [mode<mean<median] and [median<mode<mean] (hereinafter, referred to as a first condition), the control unit 120 may determine that to remove the clutter element from the I/Q signal.

Conversely, in a case where the result obtained by comparing the magnitudes of the plurality of signal characteristic values satisfies any one of [mean<median<mode], [median<mean<mode] and [mean<mode<median] (hereinafter, referred to as a second condition), the control unit 120 may determine that removal of the clutter element from the I/Q signal may not be performed.

In addition, the control unit 120 may estimate the skewed distribution of the I/Q signal using these signal characteristic values. That is, the control unit 120 may estimate the skewed distribution of the curve in the frequency domain of the I/Q signal through the comparison of the plurality of signal characteristic values, and determine to remove the clutter element from the I/Q signal according to the skewed direction, for example, right, of the estimated skewed distribution.

The control unit 120 may use conventional clutter filters or Hankel singular value decomposition (Hankel SVD) so as to remove the clutter element from the I/Q signal.

Figure 3:
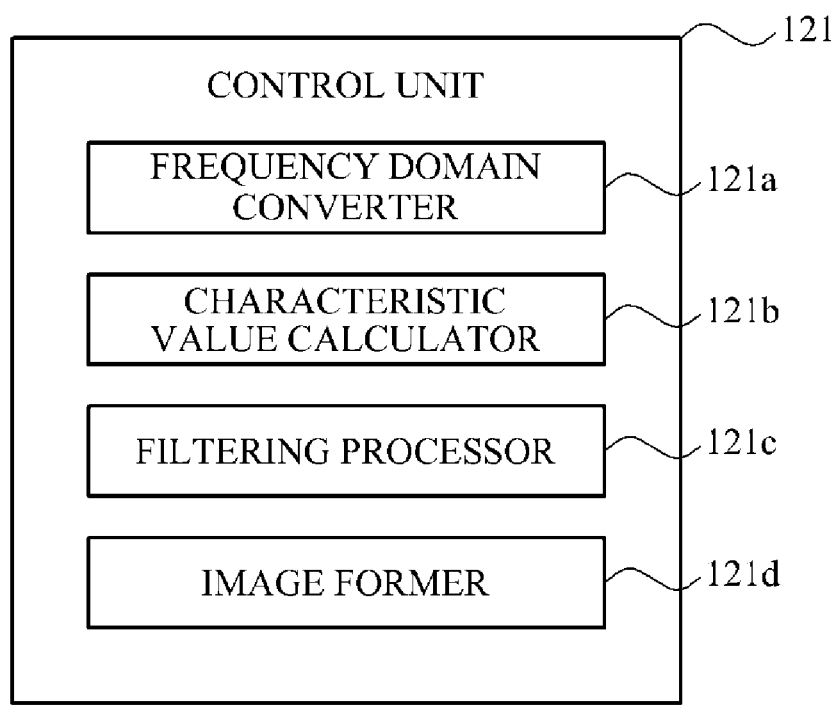
FIG. 3 is a block diagram illustrating an embodiment of a control unit of FIG. 1 using conventional clutter filters.

FIG. 3 is a block diagram illustrating an embodiment of the configuration of the control unit 120 of FIG. 1 using conventional clutter filters.

In FIG. 3, the memory 110 stores a plurality of clutter filtering procedures, and may further store indices and cutoffs respectively corresponding to the plurality of clutter filtering procedures. The indices may be sequentially graded according the magnitudes of the cutoffs.

Referring to FIG. 3, a control unit 121 may include a frequency domain converter 121a, a characteristic value calculator 121b, a filtering processor 121c and an image former 121d.

The frequency domain converter 121a performs FFT with respect to an I/Q signal for an arbitrary ensemble data in the I/Q signal outputted by the signal conversion unit 100 and then converts the I/Q signal subjected to the FFT into a frequency domain signal.

The characteristic value calculator 121b calculates a plurality of signal characteristic values based on the converted frequency domain signal.

That is, the characteristic value calculator 121b calculates the mean frequency and variance of the I/Q signal converted into the frequency domain signal by using autocorrelation. The characteristic value calculator 121b calculates signal characteristic values of the I/Q signal converted into the frequency domain signal by using the calculated mean frequency, variance and FFT order.

Figure 4A:
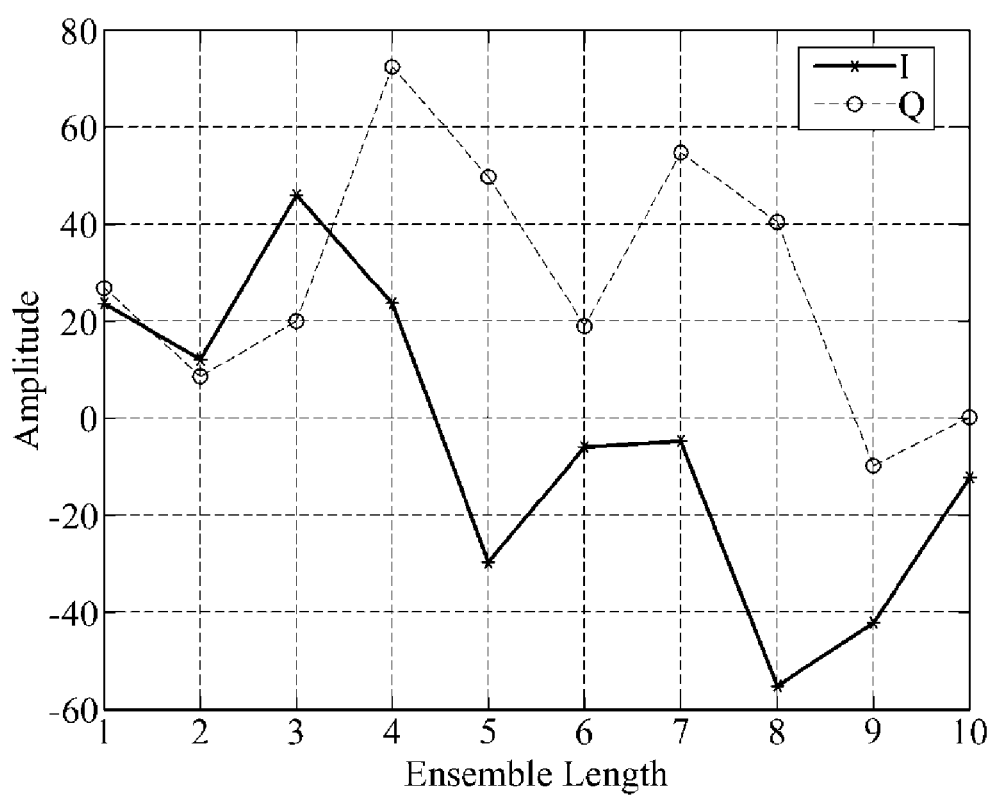
FIGS. 4A and 4B are graphs illustrating another I/Q signal converted into a frequency domain signal in the ultrasound imaging device of FIG. 1.
Figure 4B:
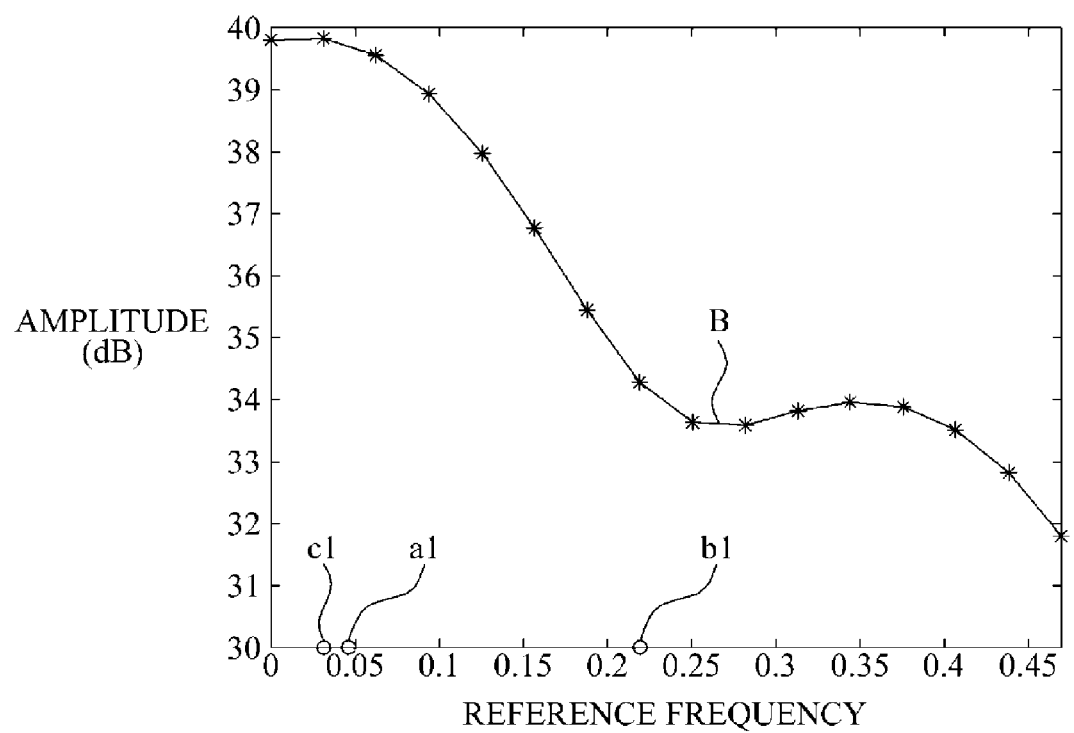

FIGS. 4A and 4B are graphs illustrating the I/Q signal converted into a frequency domain signal and its signal characteristic values, In particular, FIG. 4A shows data calculated using an autocorrelation method widely used in an ultrasound system, and FIG. 4B shows an FFT result for an ensemble data as illustrated with reference to FIG. 4A.

The median value may use a median value of all values on the x-axis (frequency domain) on the graph of FIG. 4B, obtained by performing the FFT with the graph of FIG. 4A. The mode value uses a value on the x-axis (frequency domain), which has the greatest value on the y-axis (magnitude).

Referring to FIG. 4B, the I/Q signal of the ensemble number has a mean value at frequency a1, a median value at frequency b1, and a mode value at frequency c1.

In particular, since the maximum value on the x-axis (frequency domain) is 0.47, the median value becomes 0.235 (0.47/2). In FIG. 4B, the maximum value becomes a value on the x-axis (frequency domain), which has the maximum value (vertex), and the real value may be 0.0625. The mean value is a mean value obtained by performing autocorrelation with respect to I and Q data having the aforementioned characteristics. In the present embodiment, the mean value may be 0.0473.

Referring to FIG. 4B, the signal characteristic values a1, b1 and c1 correspond to the first condition [mode value<mean value<median value].

The filtering processor 121c determines to remove a clutter element from the I/Q signal using the plurality of signal characteristic values calculated by the characteristic value calculator 121b. In a case where removal of the clutter element from the I/Q signal may be performed, the plurality of clutter filtering procedures stored in the memory 110 are applied to the I/Q signal.

In this instance, the filtering processor 121c compares magnitudes of the plurality of signal characteristic values. In a case where the compared result satisfies the first condition, the filtering processor 121c may determine to remove the clutter element from the I/Q signal.

When the filtering processor 121c determines to remove the clutter element from the I/Q signal, the filtering processor 121c applies clutter filtering of a predetermined index or cutoff to the I/Q signal. In a case where the clutter filtering of the predetermined index has been previously applied to the I/Q signal, the filtering processor 121c applies clutter filtering of the next index to the I/Q signal.

Conversely, in a case where the compared result does not satisfy the first condition, the filtering processor 121c determines not to remove the clutter element from the I/Q signal, and does not apply clutter filtering to the I/Q signal.

In another embodiment, when the compared result does not satisfy the first condition, the filtering processor 121c may determine to remove the clutter element from the I/Q signal, and apply clutter filtering of the lowest cutoff to the I/Q signal.

The image former 121d forms a color flow image of the ultrasound image using the I/Q signal finally filtered by the filtering processor 121c and then provides the formed color flow image to the display unit 140.

In addition, the control unit 120 may performs the clutter filtering of the I/Q signal by using the Hankel SVD.

Here, the control unit 120 generates a plurality of sub-matrices by performing singular value decomposition with respect to the I/Q signal converted by the signal conversion unit 100, and selects a sub-matrix that may be disregarded when performing clutter filtering among the plurality of sub-matrices based on a plurality of signal characteristics for each of the plurality of sub-matrices. Then, the control unit 120 forms the color flow image of the ultrasound image by using the selected sub-matrix.

Figure 5:
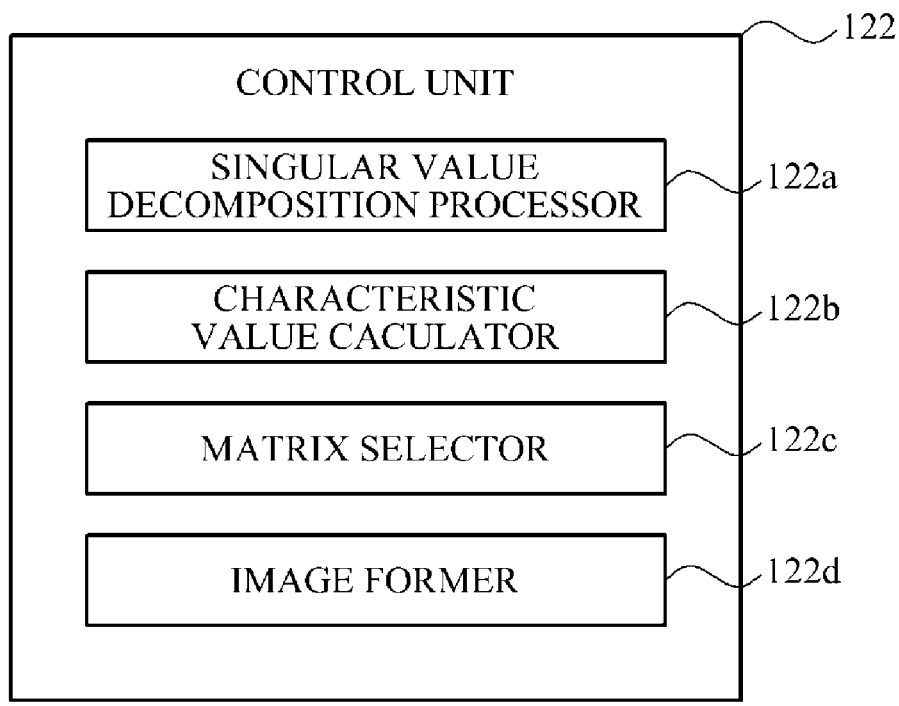
FIG. 5 is a block diagram illustrating another embodiment of the control unit of FIG. 1.

FIG. 5 is a block diagram illustrating another embodiment of the control unit 120 of FIG. 1.

Referring to FIG. 5, a control unit 120 may include a singular value decomposition processor 122a, a characteristic value calculator 122b, a matrix selector 122c and an image former 122d.

The singular value decomposition processor 122a performs singular value decomposition with the I/Q signal converted by the signal conversion unit 100, and generates a plurality of sub-matrices for the decomposed I/Q signal.

The characteristic value calculator 122b performs FFT with respect to each of the plurality of sub-matrices generated by the singular value decomposition processor 122a, and calculates a plurality of signal characteristics corresponding to each of the sub-matrices by using each of the converted data.

Figure 6:
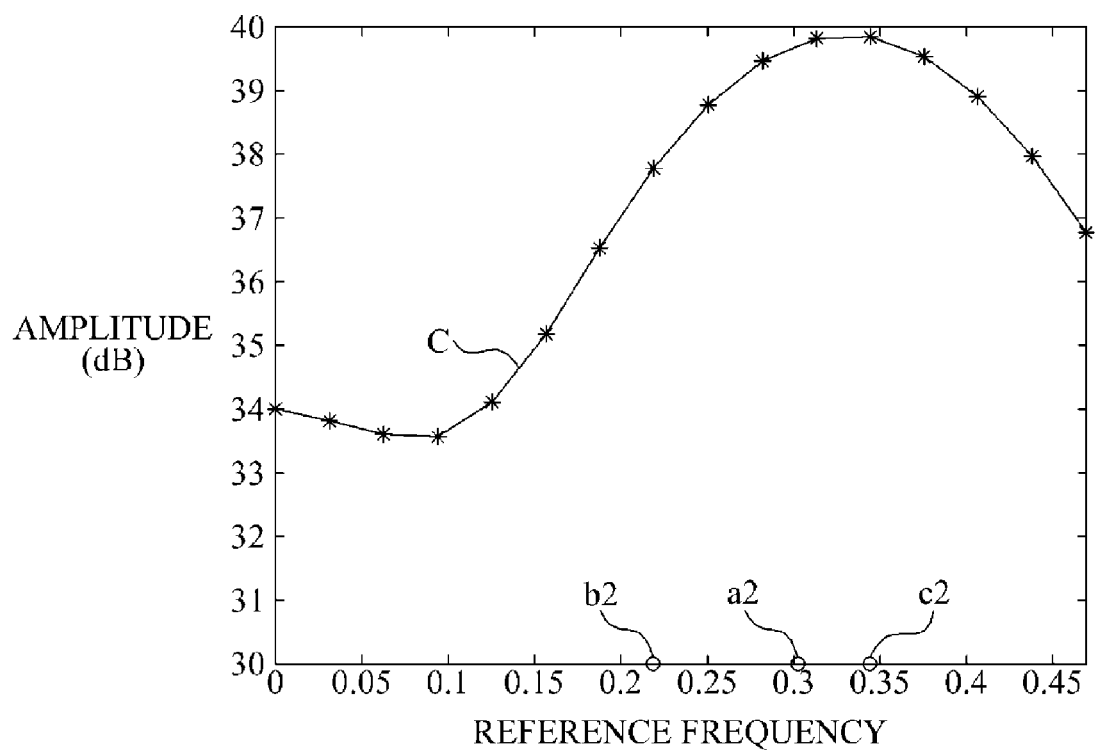
FIG. 6 is a graph illustrating still another I/Q signal converted into a frequency domain signal in the ultrasound imaging device according to the embodiment of the present invention.

FIG. 6 illustrates a graph of an arbitrary sub-matrix converted into a frequency domain sub-matrix and its signal characteristic values.

Referring to FIG. 6, there can be seen reference frequencies (Norm.Freq) and magnitudes (dB) for the sub-matrix converted into the frequency domain sub-matrix. Here, the sub-matrix has signal characteristic values of a mean value at frequency a2, a median value at frequency b2 and a mode value at frequency c2. Referring to FIG. 6, the signal characteristic values a2, b2 and c2 satisfy the second condition [median value<mean value<mode value].

The matrix selector 122c selects a sub-matrix that may be disregarded when performing the clutter filtering among the plurality of sub-matrices based on the plurality of the signal characteristic values a2, b2 and c2 calculated by the characteristic value calculator 122b and the second condition.

That is, the matrix selector 122c may compare magnitudes of the plurality of signal characteristic values for each of the plurality of sub-matrices, and select the sub-matrix that may be disregarded when performing the clutter filtering among the plurality of sub-matrices based on whether the compared result corresponds to the second condition.

The image former 122d forms a color flow image of the ultrasound image by using the sub-matrix selected by the matrix selector 122c and then provides the formed color flow image to the display unit 140.

In addition, the user input unit 130 provides an interface for receiving user's input information. In this embodiment, the interface enables a user to select information on the size and position of a target area, that is, color box, set on a brightness mode (B mode) image of an object. The user input unit 130 may include a control panel, a mouse, a keyboard, and the like.

The display unit 140 displays the color flow image formed by the control unit 120 on a user's screen.

Consequently, referring to FIG. 3, the color flow image is formed after the clutter filtering is repeatedly performed with respect to the I/Q signal several times or the color flow image is formed due to the sub-matrices that may be disregarded when performing the clutter filtering. Thus, more precise ultrasound images may be displayed and provided to the user.

Figure 7:
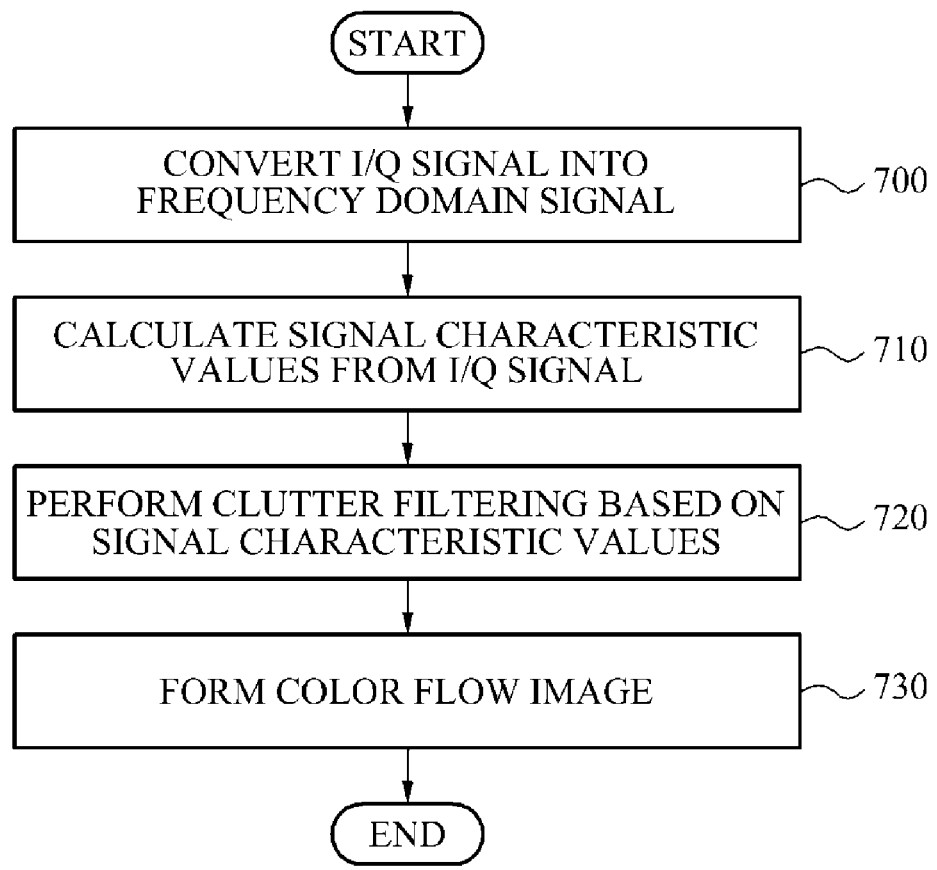
FIGS. 7 and 8 are flowcharts illustrating an ultrasound imaging method according to an embodiment of the present invention.
Figure 8:
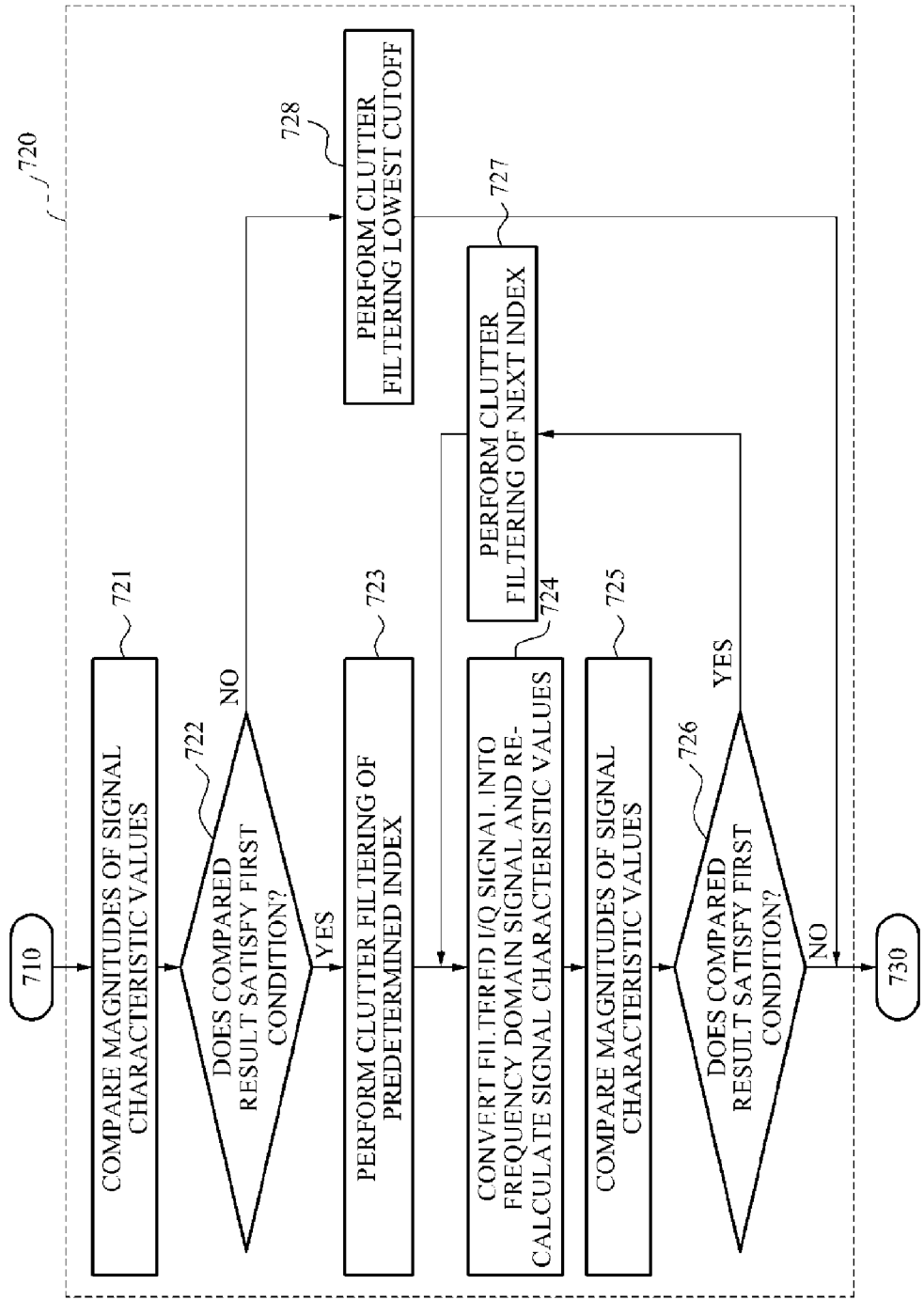

FIGS. 7 and 8 are flowcharts illustrating an ultrasound imaging method according to an embodiment of the present invention. In this case, a control unit of a device for performing the ultrasound imaging method uses conventional clutter filters. A memory of the device stores a plurality of clutter filtering procedures, and further stores indices and cutoffs respectively corresponding to the plurality of clutter filtering procedures.

Referring to FIG. 7, in operation 700, an ultrasound signal is transmitted to an object, and the ultrasound signal reflected from the object is converted into an I/Q signal. In operation 700, FFT is performed with respect to an I/Q signal for an arbitrary ensemble data in the converted I/Q signal.

In operation 710, a plurality of signal characteristic values are calculated from the I/Q signal converted in operation 700. In this instance, the signal characteristic values include a mean value, a median value, and a mode value of the I/Q signal.

In operation 720, removal of a clutter element from the I/Q signal based on the signal characteristic values calculated in operation 710 is performed. In a case where removal of the clutter element from the I/Q signal is performed, clutter filtering is applied to the I/Q signal.

In this instance, operation 720 may include a plurality of operations illustrated with reference to FIG. 8.

Referring to FIG. 8, in operation 721, magnitudes of the plurality of signal characteristic values calculated in operation 710 are compared with one another.

In operation 722, whether the result compared in operation 721 satisfies a predetermined first condition is determined. Here, the first condition means that the result obtained by comparing the magnitudes of the plurality of signal characteristic values satisfies any one of [mode<median<mean], [mode<mean<median] and [median<mode<mean].

In a case where the compared result satisfies the first condition in operation 722, clutter filtering of a predetermined index is applied to the I/Q signal in operation 723.

In operation 724, the I/Q signal filtered in operation 723 is converted into a frequency domain signal by performing FFT performs with respect to the I/Q signal, and a plurality of signal characteristic values are re-calculated.

In operation 725, the plurality of signal characteristic values re-calculated in operation 724 are compared with one another. In operation 726, whether the result compared in operation 725 satisfies the first condition is determined.

In a case where the result compared in operation 725 satisfies the first condition in operation 726, clutter filtering of the next index is re-applied to the I/Q signal to which the previous clutter filtering has been previously applied.

In addition, in a case the compared result does not satisfy the first condition in operation 722, removal of at least a clutter element from the I/Q signal is performed in operation 728, and clutter filtering of the lowest cutoff is applied to the I/Q signal.

Consequently, in operations 721 to 728, the clutter filtering is repeatedly performed until the I/Q converted in operation 700 satisfies the predetermined first condition.

In operation 730, a color flow image of an ultrasound image is formed using the I/Q signal finally filtered in operation 720, and the formed color flow image is displayed.

Accordingly, the color flow image displayed in operation 730 is formed by signals of clutter elements are removed by the clutter filtering procedures repeated one or more times, so that the device of the ultrasound imaging method can provide more precise ultrasound images to the user.

FIGS. 9 and 10 are flowcharts illustrating an ultrasound imaging method according to another embodiment of the present invention. In the ultrasound imaging method, a clutter element is removed from the I/Q signal by using the Hankel SVD.

Referring to FIG. 9, in operation 900, an ultrasound signal is transmitted to an object, and the ultrasound signal reflected from the object is converted into an I/Q signal. In operation 900, singular value decomposition is performed with respect to the converted I/Q signal.

In operation 910, a plurality of sub-matrices are generated from the I/Q signal subjected to the singular value decomposition.

In operation 920, a plurality of signal characteristic values are calculated with respect to each of the plurality of sub-matrices generated in operation 910, and a sub-matrix that may be disregarded when performing clutter filtering among the a plurality of sub-matrices is selected based on the plurality of signal characteristic values.

In this instance, operation 920 may include a plurality of operations illustrated with reference to in FIG. 10.

Referring to FIG. 10, in operation 921, each of the plurality of sub-matrices is converted into a frequency domain sub-matrix through FFT.

In operation 922, a plurality of signal characteristic values are calculated from each of the sub-matrices converted in operation 921. Here, the plurality of signal characteristic values include a mean value, a median value, and a mode value of each of the sub-matrices.

In operation 923, magnitudes of the plurality of signal characteristic values calculated in operation 922 are compared with one another. In operation 924, whether the result compared in operation 923 satisfies a predetermined second condition is determined. In this instance, the second condition means that the result obtained by comparing the magnitudes of the plurality of signal characteristic values satisfies any one of [mean<median<mode], [median<mean<mode] and [mean<mode<median].

In a case where the compared result satisfies the second condition is determined in operation 924, in operation 925, the sub-matrix corresponding to the compared result that satisfies the second condition is selected as a sub-matrix that may be disregarded when performing clutter filtering. Conversely, in a case where the compared result does not satisfy the second condition, in operation 925, the sub-matrix corresponding to the compared result that does not satisfy the second condition is not selected.

In operation 925, the signal characteristic values of each of the sub-matrices are all compared and processed in operation 923. In a case where the sub-matrices are not all processed, operation 923 is re-performed. At the re-performed operation 923, magnitudes of the signal characteristic values of the next sub-matrix are compared with one another.

Consequently, in operations 921 to 925, sub-matrices that may be disregarded when performing the clutter filtering among the plurality of sub-matrices can be selected based on the plurality of signal characteristic values for each of the plurality of sub-matrices.

In addition, in operation 930, a color flow image of an ultrasound image is formed and displayed using the sub-matrices selected in operation 920.

Accordingly, the color flow image displayed in operation 930 is formed due to the sub-matrices that may be disregarded when performing the clutter filtering among the plurality of sub-matrices of the I/Q signal, so that the device of the ultrasound imaging method can provide more precise ultrasound image to the user.

As described above, according to embodiments of the present invention, clutter filtering is performed with respect to an I/Q signal or a sub-matrix of the I/Q signal is selected based on a signal characteristic values of an ultrasound signal reflected from the an object, so that a more precise image of the ultrasound signal can be provided to a user.

Also, the embodiments of the present invention can all be applied to a conventional filtering method, a singular value decomposition method and an eigen-decomposition method.

The above-described exemplary embodiments of the present invention may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as ROM, RAM, flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments of the present invention, or vice versa.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. An ultrasound imaging device, comprising:
a signal converter configured to transmit an ultrasound signal to an object, receive the ultrasound signal reflected from the object, and convert the received ultrasound signal into an in-phase/quadrature-phase (I/Q) signal corresponding to each pixel of an image in an ultrasound image; and
a controller configured to convert the I/Q signal into a frequency domain signal, estimate a skewed distribution of the converted I/Q signal by comparing a first one of a plurality of signal characteristic values of the converted I/Q signal with a second one of the plurality of signal characteristic values of the converted I/Q signal, and determine whether or not to remove a clutter element from the I/Q signal based on the estimated skewed distribution of the converted I/Q signal,
wherein the controller is configured to generate a plurality of sub-matrices by performing singular value decomposition with respect to the I/Q signal converted by the signal converter, select a sub-matrix that is disregarded when performing the clutter filtering among the plurality of sub-matrices based on the plurality of signal characteristic values for each of the plurality of sub-matrices, and form a color flow image of the ultrasound image using the selected sub-matrix,
wherein:
the plurality of signal characteristic values comprise a mean value, a median value, and a mode value of each of the plurality of sub-matrices,
the controller is configured to compare the plurality of signal characteristic values of each of the plurality of sub-matrices with one another, and
when a result of the comparison satisfies at least one of conditions [mean value<median value<mode value], [median value<mean value<mode value] and [mean value<mode value<median value], the controller is configured to select the sub-matrix that satisfies the condition as a sub-matrix that is disregarded when removing the clutter element from the I/Q signal.

2. An ultrasound imaging method, comprising:
transmitting an ultrasound signal to an object and converting the ultrasound signal reflected from the object into an I/Q signal;
performing singular value decomposition with respect to the I/Q signal, and generating a plurality of sub-matrices;
converting each of the plurality of sub-matrices into a frequency domain sub-matrix and calculating a plurality of signal characteristic values for each of the plurality of sub-matrices;
estimating a skewed distribution of the converted I/Q signal by comparing a first one of the plurality of signal characteristic values of the converted I/Q signal with a second one of the plurality of signal characteristic values of the converted I/Q signal, and selecting a sub-matrix that is disregarded when removing a clutter element from the I/Q signal among the plurality of sub-matrices based on the estimated skewed distribution; and
forming a color flow image of an ultrasound image using the selected sub-matrix, wherein the plurality of signal characteristic values comprise a mean value, a median value, and a mode value of each of the plurality of sub-matrices, and
wherein the selecting the sub-matrix comprises:
when a result of the comparing satisfies at least one of conditions [mean value<median value<mode value], [median value<mean value<mode value]and [mean value<mode value<median value], selecting the sub-matrix that satisfies the at least one of the conditions as the sub-matrix that is disregarded when removing the clutter element from the I/O signal.

* * * * *